United States Patent [19]
Tashiro et al.

[11] Patent Number: 5,008,410
[45] Date of Patent: Apr. 16, 1991

[54] METHOD FOR PRODUCING FURFURYL ALCOHOLS

[75] Inventors: Kazuo Tashiro, Oita; Kunihiko Tanaka, Nara, both of Japan

[73] Assignee: Sumitomo Chemical Company, Limited, Osaka, Japan

[21] Appl. No.: 053,687

[22] Filed: May 26, 1987

[30] Foreign Application Priority Data

| May 28, 1986 | [JP] | Japan | 61-122925 |
| May 28, 1986 | [JP] | Japan | 61-122926 |
| Jul. 28, 1986 | [JP] | Japan | 61-177119 |
| Jul. 28, 1986 | [JP] | Japan | 61-177120 |
| Dec. 3, 1986 | [JP] | Japan | 61-288352 |
| Dec. 3, 1986 | [JP] | Japan | 61-288353 |

[51] Int. Cl.$^5$ .................................. C07D 307/02
[52] U.S. Cl. ........................................... 549/497
[58] Field of Search ............................... 549/497

[56] References Cited

U.S. PATENT DOCUMENTS 3,992,432 11/1976 Napier et al. ............... 260/513 HX
4,352,756 10/1982 Takisawa et al. ................ 549/497

FOREIGN PATENT DOCUMENTS 0037588 10/1981 European Pat. Off. .
0113107  7/1984 European Pat. Off. .

OTHER PUBLICATIONS

Tetrahedron Letters, vol. 26, No. 11, pp. 1449–1452 (1985), Pétrier, C., J. Einhorn, and J. L. Luche.
J. Org. Chem., 1985, 50, 910–912, Pétrier, C. and J. L. Luche.

Primary Examiner—John W. Rolling
Attorney, Agent, or Firm—Stevens, Davis, Miller & Mosher

[57] ABSTRACT

A method for producing a furfuryl alcohol useful as an intermediate for producing agricultural chemicals, medicines, perfumes, etc., represented by the general formula (I),

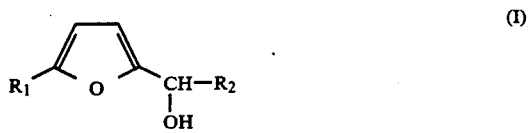

(I)

wherein $R_1$ represents a hydrogen atom or a methyl group, and $R_2$ represents an allyl or propargyl group, which comprises reacting a furfural represented by the general formula (II),

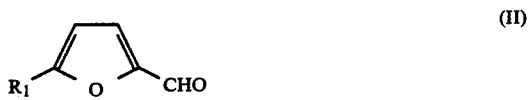

(II)

wherein $R_1$ has the same meaning as described above, with a halogen compound represented by the general formula, $$X-R_2$$

wherein X represents a halogen atom and $R_2$ has the same meaning as described above, in water or a water-/organic solvent mixed solvent in the presence of at least one organic quaternary ammonium salt selected from the group consisting of tetra($C_2$-$C_5$ alkyl)amonium halide, benzyltri ($C_2$-$C_3$ alkyl)ammonium chloride, dodecyltrimethylammonium bromide and cetyltrimethylammonium chloride as well as an inorganic ammonium salt and zinc.

10 Claims, No Drawings

METHOD FOR PRODUCING FURFURYL ALCOHOLS

The present invention relates to a method for producing a furfuryl alcohol represented by the general formula (I),

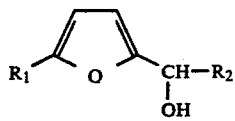

(I)

wherein $R_1$ represents a hydrogen atom or a methyl group, and $R_2$ represents an allyl or propargyl group.

A furfuryl alcohol represented by the above general formula (I) is a useful intermediate for producing agricultural chemicals, medicines, perfumes, etc.

Hitherto, for obtaining an alcohol by the reaction of a carbonyl compound with allyl halide or propargyl halide, there are well known (a) a method by Grignard reaction, (b) a method by Reformatsky reaction, (c) a method passing through an organo-lithium compound, etc.

As another method, (d) in the reaction of a carbonyl compound with allyl halide in a saturated aqueous ammonium chloride solution in the presence of zinc, there is known a method of improving the yield by carrying out said reaction in the coexistence of benzyltrimethylammonium chloride [J. Org. Chem.,50, 910–912 (1985)].

All of the above methods (a) to (c), however, require a non-aqueous condition which is very disadvantageous industrially, and are accompanied by generation of a large quantity of reaction heat. Particularly, the methods (a) and (b), in carrying them out on industrial scales, had problems that they are accompanied by great difficulties such as rapid heat generation and there being a necessity to pass through an inflammable intermediate.

Also, when the method (d) is applied to the reaction of allyl halide with furfural or 5-methylfurfural, an improvement in the yield owing to the coexistence of benzyltrimethylammonium chloride is little observed, so that this method is very unsatisfactory as an industrial method for producing furfuryl alcohols represented by the foregoing general formula (I).

For this reason, the present inventors extensively studied to improve the foregoing defects to produce furfuryl alcohols represented by the general formula (I) industrially advantageously, and as a result, found that the desired furfuryl alcohols can be obtained in a short time and in a high yield by reacting a furfural with allyl halide or propargyl halide in water or a water/organic solvent mixed solvent in the presence of a particular organic quaternary ammonium salt, an inorganic ammonium salt and zinc. The present inventors thus attained to the present invention.

The present invention provides a method for producing a furfuryl alcohol represented by the foregoing general formula (I) which comprises reacting a furfural represented by the general formula (II),

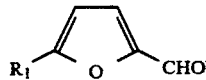

(II)

wherein $R_1$ represents a hydrogen atom or a methyl group, with a halogen compound represented by the general formula, $$X-R_2$$

wherein X represents a halogen atom, and $R_2$ represents an allyl or propargyl group, in water or a water/organic solvent mixed solvent in the presence of at least one organic quaternary ammonium salt selected from the group consisting of tetra($C_2$–$C_5$ alkyl)ammonium halide, benzyltri($C_2$–$C_3$ alkyl)ammonium chloride, dodecyltrimethylammonium bromide and cetyltrimethylammonium chloride as well as an inorganic ammonium salt and zinc.

In the present invention, a furfural used as a material includes furfural and 5-methylfurfural, and the halogen compound includes allyl halides (e.g. allyl chloride, allyl bromide) and propargyl halides (e.g. propargyl chloride, propargyl bromide).

The amount of zinc used is in a range of from 1 to 5 times by mole based on a furfural which is a material.

A preferred inorganic ammonium salt used in this reaction includes ammonium halides such as ammonium chloride, ammonium bromide, etc. The amount of the salt used is generally from 0.05 to 1 time by weight based on the reaction solvent described later. This reaction of course proceeds if the amount exceeds 1 time by weight, but the slurry concentration, increases, being industrially disadvantageous. Similarly, the reaction proceeds if the amount is less than 0.05 time by weight, but a long period of time is required to complete the reaction, being industrially disadvantageous.

For the organic quaternary ammonium salt, there is used at least one member selected from the group consisting of tetra($C_2$–$C_5$ alkyl)ammonium halides (e.g. tetraethylammonium bromide, tetraethylammonium chloride, tetrapropylammonium bromide, tetrapropylammonium chloride, tetrabutylammonium bromide, tetrabutylammonium chloride, tetrabutylammonium iodide, tetrapentylammonium bromide, tetrapentylammonium chloride), benzyltri($C_2$–$C_3$ alkyl)-ammonium chlorides (e.g. benzyltriethylammonium chloride, benzyltripropylammonium chloride), dodecyltrimethylammonium bromide and cetyltrimethylammonium chloride. Other organic quaternary, ammonium salts than those described above give no sufficient effect.

The amount of these organic quaternary ammonium salts used is preferably in a range of from 0.005 to 1 time by mole based on a furfural used as a material. This reaction of course proceeds if the amount exceeds 1 time by mole, but this brings about an increase in the material cost, being uneconomical.

The reaction is carried out in a water solvent or a water/organic solvent mixed system. The organic solvent is selected from the group consisting of aliphatic hydrocarbons, aromatic hydrocarbons, ethers and amines, and preferably it includes n-hexane, toluene, xylene, tetrahydrofuran, diethyl ether and pyridine. The amount of the solvent used is not particularly limited, but generally it is from 1 to 50 times by weight for the water solvent, and from 0 to 30 times by weight for the organic solvent based on a furfural, a material.

The amount of the halogen compound used is generally from 1 to 5 times by mole based on a furfural, a material.

The reaction method may be any of the following methods: (1) A method in which the inorganic ammonium salt (as an aqueous solution in many cases) is added in portions to a mixture comprising a furfural, halogen compound, organic quaternary ammonium salt, zinc and reaction solvent, and (2) a method in which the halogen compound is added in portions to a mixture comprising a furfural, organic quaternary ammonium salt, inorganic ammonium salt, zinc and reaction solvent. However, the method (2) is superior in terms of yield, being more advantageous as an industrial method.

In this case, the addition may be carried out either continuously or intermittently. A time required for the addition is generally in a range of from 30 minutes to 5 hours, but it is not particularly limited. A too short time, however, causes a reduction in the yield, being generally disadvantageous.

The reaction temperature is in a range of, generally, from 0° to 100° C., preferably from 5° to 80° C.

The progress of the reaction can be followed by means of mechanical analysis such as gas chromatography, and the reaction comes to an end at a point when all the furfural used as a material have disappeared. The furfuryl alcohol thus obtained is separated from the reaction solution, for example, by separating the organic layer from the aqueous layer and distilling the former layer.

Thus, according to the method of the present invention, the desired furfuryl alcohols represented by the foregoing general formula (I) can be obtained industrially easily and in a short time.

The present invention will be illustrated with reference to the following examples.

EXAMPLE 1

44 Grams of 5-methylfurfural, 36.7 g of allyl chloride, 31.4 g of zinc powder, 28 g of tetrapentylammonium chloride and 440 g of water were added to a flask, and an aqueous ammonium chloride solution comprising 95 g of ammonium chloride and 345 g of water was added dropwise thereto over 1 hour with stirring while maintaining the temperature at 45°±3° C. After completion of the addition, the reaction solution was kept at the same temperature for 2 hours.

After completion of the reaction, the reaction solution was separated into an aqueous and organic layers, and the organic layer was rectified under reduced pressure to obtain 51.4 g of the fraction of 2-(1-hydroxy-3-butenyl)-5-methylfuran (content, 99.4%) (yield, 83.9%).

COMPARATIVE EXAMPLE 1

Reaction and after-treatment were carried out in the same manner as in Example 1 except that an equimolar amount of benzyltrimethylammonium chloride was used in place of tetrapentylammonium bromide, to obtain 42.7 g of the fraction of 2-(1-hydroxy-3-butenyl)-5-methylfuran (content, 99.2%) (yield, 69;6%).

When no organic ammonium salt was used, the yield was 69.0%.

EXAMPLE 2

38.4 Grams of furfural, 58.1 g of allyl bromide, 52.3 g of zinc powder, 26 g of tetrabutylammonium bromide, 440 g of water and 88 g of toluene were added to a flask, and an aqueous ammonium chloride solution comprising 95 g of ammonium chloride and 345 g of water was added dropwise thereto over 1 hour with stirring while maintaining the temperature at 35°±3° C. After completion of the addition, the reaction solution was kept at the same temperature for 2 hours.

After completion of the reaction, the reaction solution was separated into an aqueous and organic layers, and the organic layer was rectified under reduced pressure to obtain 46.0 g of the fraction of 2-(1-hydroxy-3-butenyl)furan (content, 99.2%) (yield, 82.6%).

COMPARATIVE EXAMPLE 2

Reaction and after-treatment were carried out in the same manner as in Example 2 except that an equimolar amount of benzyltrimethylammonium chloride was used in place of tetrabutylammonium bromide, to obtain 20.2 g of the fraction of 2-(1-hydroxy-3-butenyl)furan (content, 99.0%) (yield, 36.2%).

When no organic ammonium salt was used, the yield was 20.5%.

EXAMPLE 3

44 Grams of 5-methylfurfural, 52.3 g of zinc powder, 26 g of tetrabutylammonium bromide, 88 g of ammonium chloride, 88 g of toluene and 792.8 g of water were added to a flask, and 61.2 g of allyl chloride was added dropwise thereto over 1 hour with stirring while maintaining the temperature at 40°±2° C. After completion of the addition, the reaction solution was kept at the same temperature for 2 hours.

After completion of the reaction, the reaction solution was separated into an aqueous and organic layers, and the organic layer was rectified under reduced pressure to obtain 57.5 g of the fraction of 2-(1-hydroxy-3-butenyl)-5-methylfuran (content, 99.6%) (yield, 94.1%).

EXAMPLE 4

44 Grams of 5-methylfurfural, 52.3 g of zinc powder, 28 g of tetrapentylammonium chloride, 88 g of ammonium chloride, 55 g of toluene and 814.8 g of water were added to a flask, and 58.1 g of allyl bromide was added dropwise thereto over 2 hours with stirring while maintaining the temperature at 45°±2° C. After completion of the addition, the reaction solution was kept at the same temperature for 2 hours.

After completion of the reaction, the reaction solution was separated into an aqueous and organic layers, and the organic layer was rectified under reduced pressure to obtain 57.0 g of the fraction of 2-(1-hydroxy-3-butenyl)-5-methylfuran (content, 99.7%) (yield, 93.4%).

EXAMPLE 5

Reaction and after-treatment were carried out in the same manner as in Example 3 except that an equimolar amount of furfural was used in place of 5-methylfurfural, and that ammonium bromide and tetrahydrofuran were used in place of ammonium chloride and toluene, respectively, in the same weights as those of the latter, to obtain 50.6 g of the fraction of 2-(1-hydroxy-3-butenyl)-furan (content, 99.3%) (yield, 91.0%).

EXAMPLES 6 to 14

Reaction and after-treatment were carried out in the same manner as in Example 3 except that an equimolar amount of the organic ammonium salts shown in Table 1 was used in place of tetrabutylammonium bromide, to obtain 2-(1-hydroxy-3-butenyl)-5-methylfuran in the yield shown in Table 1.

TABLE 1

| Example | Organic ammonium salt | Yield (%) |
|---|---|---|
| 6 | Tetraethylammonium bromide | 90.5 |
| 7 | Tetraethylammonium chloride | 90.1 |

TABLE 1-continued

| Example | Organic ammonium salt | Yield (%) |
|---|---|---|
| 8 | Tetrapropylammonium bromide | 90.9 |
| 9 | Tetrapropylammonium chloride | 90.6 |
| 10 | Tetrabutylammonium chloride | 93.5 |
| 11 | Tetrabutylammonium iodide | 94.2 |
| 12 | Benzyltriethylammonium chloride | 90.8 |
| 13 | Benzyltripropylammonium chloride | 93.0 |
| 14 | Dodecyltrimethylammonium bromide | 92.1 |

EXAMPLE 15

44 Grams of 5-methylfurfural, 35.8 g of propargyl chloride, 31.4 g of zinc powder, 28 g of tetrapentylammonium chloride and 440 g of water were added to a flask, and an aqueous ammonium chloride solution comprising 95 g of ammonium chloride and 345 g of water was added dropwise thereto over 1 hour with stirring while maintaining the temperature at 30°±3° C. After completion of the addition, the reaction solution was kept at the same temperature for 2 hours.

After completion of the reaction, the reaction solution was separated into an aqueous and organic layers, and the organic layer was rectified under reduced pressure to obtain 48.4 g of the fraction of 2-(1-hydroxy-3-butynyl)-5-methylfuran (content, 99.6%) (yield, 80.3%).

EXAMPLE 16

44 Grams of 5-methylfurfural, 57.1 g of propargyl bromide, 52.3 g of zinc powder, 26 g of tetrabutylammonium bromide, 88 g of toluene and 440 g of water were added to a flask, and an aqueous ammonium chloride solution comprising 95 g of ammonium chloride and 345 g of water was added dropwise thereto over 1 hour with stirring while maintaining the temperature at 35°±3° C. After completion of the reaction, the reaction solution was kept at the same temperature for 2 hours.

After completion of the reaction, the reaction solution was separated into an aqueous and organic layers, and the organic layer was rectified under reduced pressure to obtain 50.7 g of the fraction of 2-(1-hydroxy-3-butynyl)-5-methylfuran (content, 99.7%) (yield, 84.2%).

EXAMPLE 17

Reaction and after-treatment were carried out in the same manner as in Example 16 except that an equimolar amount of furfural was used in place of 5-methylfurfural, and that cetyltrimethylammonium chloride and tetrahydrofuran were used in place of tetrabutylammonium bromide and toluene, respectively, in the same weights as those of the latter, to obtain 44.0 g of the fraction of 2-(1-hydroxy-3-butynyl)furan (content, 99.4%) (yield, 80.3%).

EXAMPLE 18

44 Grams of 5-methylfurfural, 52.3 g of zinc powder, 26 g of tetrabutylammonium bromide, 88 g of ammonium chloride, 88 g of toluene and 792.8 g of water were added to a flask, and 59.6 g of propargyl chloride was added dropwise thereto over 1 hour with stirring while maintaining the temperature at 35°±2° C. After completion of the addition, the reaction solution was kept at the same temperature for 2 hours.

After completion of the reaction, the reaction solution was separated into an aqueous and organic layers, and the organic layer was rectified under reduced pressure to obtain 56.6 g of the fraction of 2-(1-hydroxy-3-butynyl)-5-methylfuran (content, 99.6%) (yield, 93.8%).

EXAMPLE 19

44 Grams of 5-methylfurfural, 47.1 g of zinc powder, 28 g of tetrapentylammonium chloride, 66 g of ammonium chloride, 66 g of toluene and 814.8 g of water were added to a flask, and 62.8 g of propargyl bromide was added dropwise thereto over 1 hour with stirring while maintaining the temperature at 40°±2° C. After completion of the addition, the reaction solution was kept at the same temperature for 2 hours.

After completion of the reaction, the reaction solution was separated into an aqueous and organic layers, and the organic layer was rectified under reduced pressure to obtain 54.9 g of the fraction of 2-(1-hydroxy-3-butynyl-)5-methylfuran (content, 99.7%) (yield, 91.1%).

EXAMPLE 20

Reaction and after-treatment were carried out in the same manner as in Example 18 except that an equimolar amount of furfural was used in place of 5-methylfurfural, and that cetyltrimethylammonium chloride and tetrahydrofuran were used in place of tetrabutylammonium bromide and toluene, respectively, in the same weights as those of the latter, to obtain 50.1 g of the fraction of 2-(1-hydroxy-3-butynyl)furan (content, 99.4%) (yield, 91.4%).

EXAMPLE 21

Reaction and after-treatment were carried out in the same manner as in Example 18 except that 45.5 g of ammonium bromide and 44 g of tri-n-butylamine were used in place of ammonium chloride and toluene, respectively, to obtain 54.5 g of the fraction of 2-(1-hydroxy-3-butynyl)-5-methylfuran (content, 99.7%) (yield, 90.5%).

What is claimed is:

1. A method for producing a furfuryl alcohol represented by the general formula (I),

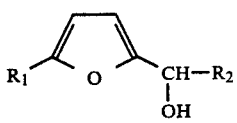

(I)

wherein $R_1$ represents a hydrogen atom or a methyl group and $R_2$ represents an allyl or propargyl group, which comprises reacting a furfural represented by the general formula (II),

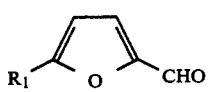

(II)

wherein $R_1$ has the same meaning as described above, with a halogen compound represented by the general formula, $$X-R_2$$

wherein X represents a halogen atom and $R_2$ has the same meaning as described above, in water or a water-/organic solvent mixed system, in the presence of at least one organic quaternary ammonium salt selected from the group consisting of tetra($C_2$-$C_5$ alkyl)ammonium halide, benzyltri($C_2$-$C_3$ alkyl)ammonium chloride, dodecyltrimethyl-ammonium bromide and cetyltrimethylammonium chloride as well as an inorganic ammonium salt and zinc.

2. A method according to claim 1, wherein the amount of the halogen compound used is in a range of from 1 to 5 times by mole based on a furfural.

3. A method according to claim 1, wherein the amount of zinc used is in a range of from 1 to 5 times by mole based on a furfural.

4. A method according to claim 1, wherein the amount of the organic quaternary ammonium salt used is in a range of from 0.005 to 1 time by mole based on a furfural.

5. A method according to claim 1, wherein the amount of the inorganic ammonium salt used is from 0.05 to 1 time by weight based on the reaction solvent.

6. A method according to claim 1, wherein the amount of water used is from 1 to 50 times by weight based on a furfural, and that of the organic solvent used is from 0 to 30 times by weight based on, a furfural.

7. A method according to claim 1, wherein the inorganic ammonium salt is ammonium halide.

8. A method according to claim 1, wherein the organic solvent is at least one member selected from the group consisting of aromatic hydrocarbons, aliphatic hydrocarbons, ethers and amines.

9. A method according to claim 8, wherein the organic solvent is n-hexane, toluene, xylene, tetrahydrofuran, diethyl ether or pyridine.

10. A method according to claim 1, wherein reaction is carried out while adding the halogen compound to the reaction system in portions.

* * * * *